(12) United States Patent
Despa et al.

(10) Patent No.: US 9,901,672 B2
(45) Date of Patent: Feb. 27, 2018

(54) SMART PORTABLE INFUSION PUMP

(71) Applicant: Becton, Dickinson and Company, Franklin Lakes, NJ (US)

(72) Inventors: Mircea Stefan Despa, Cary, NC (US); Adam Martin, Holly Springs, NC (US); Sundeep Kankanala, Chapel Hill, NC (US); Austin McKinnon, Herriman, UT (US); Christian Sandmann, Wayne, NJ (US); Ralph Sonderegger, Farmington, UT (US); Ray Isaacson, Layton, UT (US); Marcel Souza, Lehi, UT (US); Bart Peterson, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 96 days.

(21) Appl. No.: 15/004,828

(22) Filed: Jan. 22, 2016

(65) Prior Publication Data

US 2016/0213843 A1     Jul. 28, 2016

Related U.S. Application Data

(60) Provisional application No. 62/107,934, filed on Jan. 26, 2015.

(51) Int. Cl.
*A61M 5/142* (2006.01)
*A61M 5/36* (2006.01)

(52) U.S. Cl.
CPC ......... *A61M 5/14244* (2013.01); *A61M 5/365* (2013.01); *A61M 2005/14268* (2013.01); *A61M 2205/276* (2013.01); *A61M 2205/3334* (2013.01); *A61M 2205/3368* (2013.01); *A61M 2205/3553* (2013.01); *A61M 2205/3584* (2013.01); *A61M 2205/505* (2013.01);
(Continued)

(58) Field of Classification Search
CPC .............. A61M 5/14244; A61M 5/365; A61M 2005/14268; A61M 2205/276; A61M 2205/3334; A61M 2205/3368; A61M 2205/3553; A61M 2205/3584; A61M 2205/505; A61M 2205/6054; A61M 2205/6063
USPC .............................. 604/65–67, 151, 246, 506
See application file for complete search history.

(56) References Cited

U.S. PATENT DOCUMENTS

| 4,758,228 A | * | 7/1988 | Williams | ............... A61M 5/142 128/DIG. 12 |
| 5,368,562 A | * | 11/1994 | Blomquist | ............ A61M 5/172 604/246 |

(Continued)

OTHER PUBLICATIONS

International Search Report and Written Opinion dated Mar. 17, 2016, PCT application No. PCT/US2016/014470 filed Jan. 22, 2016.

*Primary Examiner* — Manuel Mendez
(74) *Attorney, Agent, or Firm* — Knobbe, Martens, Olson & Bear, LLP

(57) ABSTRACT

Described herein is a programmable portable infusion device. The infusion device may include electronics such as sensors, and can be programmed to detect parameters related to the proper administration of infusion. If the sensors detect that a parameter is outside of a defined boundary or range, the infusion device may notify a user that it may not be safe to administer infusion and may prevent infusion from occurring.

21 Claims, 9 Drawing Sheets

(52) U.S. Cl.
CPC ............... *A61M 2205/6054* (2013.01); *A61M 2205/6063* (2013.01)

(56) References Cited

U.S. PATENT DOCUMENTS

| | | | | |
|---|---|---|---|---|
| 6,162,194 A | * | 12/2000 | Shipp | A61M 3/0258 604/151 |
| 2004/0235446 A1 | | 11/2004 | Flaherty | |
| 2011/0144616 A1 | | 6/2011 | Michaud | |
| 2013/0331790 A1 | | 12/2013 | Brown | |
| 2014/0194817 A1 | * | 7/2014 | Lee | A61M 5/14228 604/151 |
| 2015/0025498 A1 | * | 1/2015 | Estes | A61M 5/14244 604/506 |

* cited by examiner

SMART PORTABLE INFUSION PUMP

RELATED U.S. APPLICATIONS

This application claims priority to U.S. Provisional Appl. No. 62/107,934 filed on Jan. 26, 2015, which is hereby incorporated by reference in its entirety.

BACKGROUND OF THE INVENTION

Field of the Invention

This invention relates to infusion pumps, and more particularly, relates to portable infusion pumps with smart capabilities for providing fluids to patients in need of therapeutic treatments.

Description of the Related Art

Infusion pumps are medical devices that provide delivery of measured amounts of infusates, which are fluids such as medicine or nutrients, to a patient. Infusion pumps allow for delivery of precise volumes of fluids, including very small volumes, at precise intervals or rates. Infusion pumps currently on the market have programmable interfaces that allow for customizable therapeutic treatment regimens. Existing devices can store and retrieve drug libraries and have safeguards capable of preventing gross programming errors if ineffective or life-threatening infusion parameters are attempted for a particular drug. Existing infusion pumps may also connect to the electronic medical records system of the care facility in which they operate.

However, the complexity of a typical infusion pump can make it difficult to use. Infusion pumps can be difficult to set up, to program, and to operate. For this reason, they generally require trained medical personnel to operate. Existing pumps also tend to be large and bulky, restricting the ability for a patient to leave a treatment area while continuing to receive care or from moving within a treatment area.

SUMMARY OF THE INVENTION

One aspect of the invention is a smart programmable infusion device that contains a driving element of an infusion pump as well as a plurality of smart modules to detect a condition of use of the infusion pump and communicate that information to a patient.

One embodiment is a device for confirming the identity of a patient, the identity of an infusate, or the dosage amount of an infusate. This aspect can be achieved by providing one or more identification sensors.

Another embodiment of the present invention is a device for preventing infusion if an infusate is not in suitable condition for infusion or if the infusion is not being administered properly. This aspect can be achieved by providing one or more sensors related to conditions affecting the infusate or of the infusion process.

Another embodiment is a method of operating a programmable infusion device comprising a plurality of smart modules.

Another embodiment of the present invention is a method of detecting the identity of a patient, the identity of an infusate, or the dosage amount of an infusate.

In another embodiment, data related to the identity of a patient, the identity of an infusate, or the dosage amount of an infusate can be transmitted to an external device.

Another embodiment is a method of detecting the condition of use of an infusate and an infusion device.

In another embodiment of the present invention, data related to the condition of use of an infusate or of an infusion device can be transmitted to an external device.

DETAILED DESCRIPTION

Figure 1A:
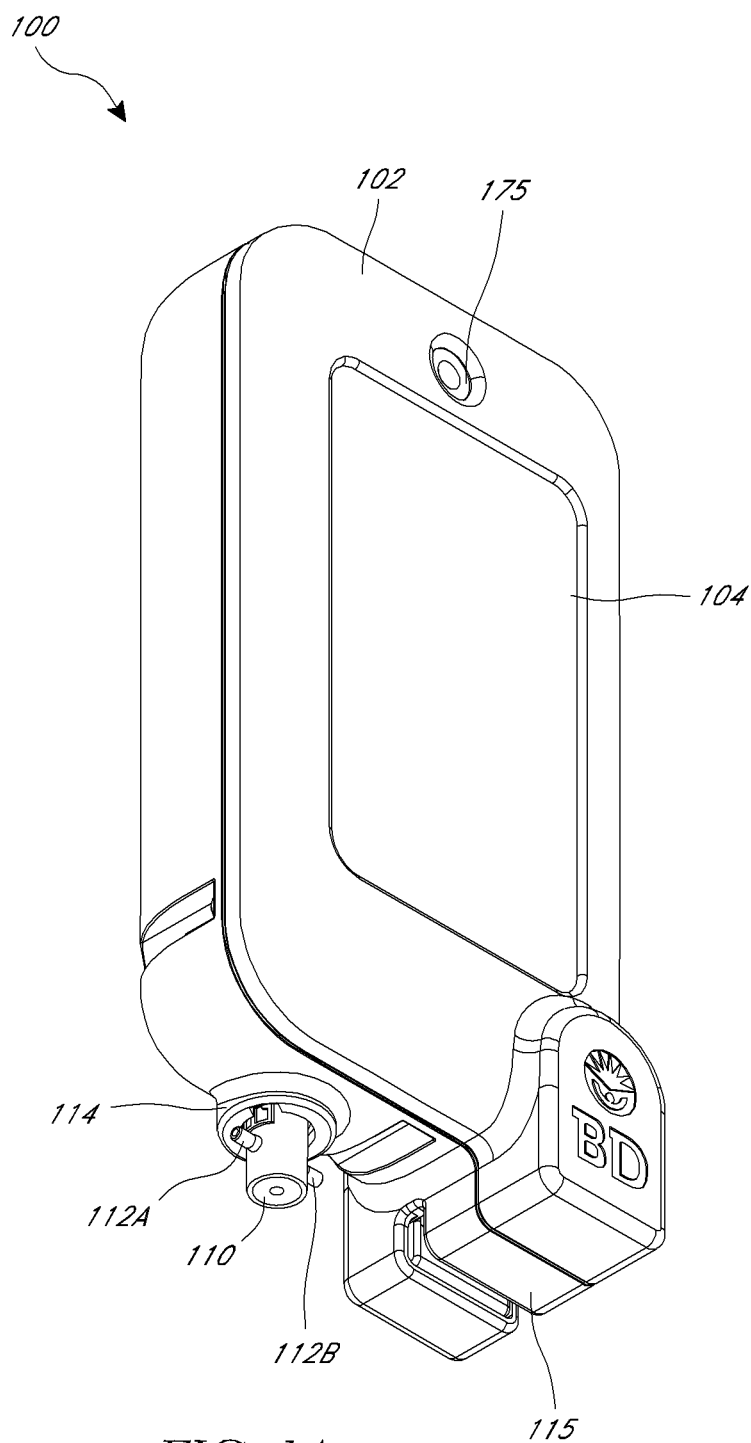
FIG. 1A depicts a front perspective view of an infusion device in accordance with an illustrative embodiment of the present invention.

As will be appreciated by one skilled in the art, there are numerous ways of carrying out the examples, improvements, and arrangements of an infusion device in accordance with embodiments of the invention disclosed herein. Although reference will be made to the illustrative embodiments depicted in the drawings and the following description, these embodiments are not meant to be exhaustive of the various alternative designs and embodiments that are encompassed by the disclosed invention. Those skilled in the art will readily appreciate that various modifications may be made, and various combinations can be made, without departing from the invention.

One embodiment of the invention is an intelligent portable infusion device that includes an integrated infusion pump in a lightweight and handheld form factor. The infusion pump may be made up of a driving element and an infusion pump head, as described in more detail below. In one embodiment, the infusion pump is a volumetric infusion pump. Such pumps may be used, among other applications, to treat patients undergoing chemotherapy.

In one embodiment, the infusion device is made of two principle components, one being a smart device such as a cellular telephone, and the other being an infusion device that is configured to pump fluids. In this embodiment, the cellular telephone may mate with the infusion device and run applications allowing the cellular telephone to control the operation of the infusion device. In one embodiment, the infusion device is a cradle that is adapted to electrically and mechanically mate with a cellular telephone. A user may then control the infusion device by inputting commands to a touch screen of the cellular telephone to thereby control the operation of the infusion device. The infusion device may include a supplemental battery to extend the useful operating time of the cellular telephone while connected to the infusion device.

In one embodiment, the infusion device may have a portable durable housing that contains a touch screen or other user interface control system for inputting and monitoring the operation of the device. Including all of the elements of an intelligent infusion pump in a small portable device allows medicament infusion to be readily administered at a medical facility, in the home, or in an ambulatory setting. The infusion device can also allow freedom of movement for a patient undergoing an infusion. The infusion device may be reusable, allowing for a clinician or emergency medical technician to treat multiple patients using the same pump.

In one illustrative embodiment, the portable durable housing contains the driving element of an intelligent infusion pump, as well as a plurality of smart modules and sensors. The portable durable housing can be configured to engage a pump head, the pump head being configured to further engage a disposable fluid path. The driving element in the portable durable housing can be configured to cause motion in the pump head, displacing fluid within the disposable fluid path. In one embodiment, the pump head may be disposable, allowing for multiple pump heads to be used with the same infusion device. The disposable feature of the pump head can decrease the risk of contamination when administering multiple fluids to multiple patients. The pump head may further be packaged as part of the disposable fluid head to allow for easy assembly and use of the infusion device. Furthermore, the driving element of the infusion device may be configured to engage and drive multiple types of pump heads.

In some embodiments, the infusion device is configured to be programmable by a user. Infusion pumps provide the delivery of a measured amount of infusates. The infusion device can comprise a user interface displayed on a touch screen for programming one or more infusion parameters. These parameters can include the fluid to be administered, amount of dose, rate of dose administration, and intervals at which the dose is to be administered. In one illustrative embodiment, the infusion device further comprises a computing module containing one or more microprocessors that receive programmed instructions from the user interface or from an external device and can transmit those instructions to the infusion driving element so that an infusion is administered according to the programmed instructions.

In an illustrative embodiment, the infusion device can include one or more environmental sensors capable of monitoring and detecting external events or characteristics associated with the use of the infusion device. Exemplary environmental sensors can be configured to measure temperature, flow, pressure, and the presence of air in fluid. The sensors may detect a state of a fluid being administered to a user. The smart device can also include a computing module configured to process data from the sensors to determine a state of the fluid being administered. Thus, the smart device can verify cold chain and drug authenticity. Once the state of the fluid is determined, the computing module may determine if the fluid is ready for infusion to a patient. If the fluid is not ready for infusion, the device can be configured with safeguards to prevent the administration of infusion if the fluid is not ready for use, or if the device is programmed to deliver a dangerous or ineffective amount of fluid.

The infusion device may further include one or more identification sensors including, but not limited to, a digital camera, a radio frequency (RF) tag reader and a bar code scanner. In some instances, the same infusion device may be used for more than one patient or more than one fluid. The identification sensors can be configured to ascertain the identity of the infusate being administered by the infusion device. If the correct infusate is not identified by the identification sensor, the infusion device may be configured to prevent administration of the infusate. An identifier, such as a bar code or RF tag can also contain dosage information. Thus, the identification sensors may also be configured to identify the dosage of the medicine about to be delivered to the user. If the correct dose is not identified by the identification sensor, the infusion device may be configured to prevent administration of the fluid.

In some embodiments, the infusion device can be configured to prevent infusion, terminate infusion, or prevent further infusion based on the occurrence of one or more predetermined events, such as, for example, determination that data from one or more environmental sensors is outside of a defined range, determination from one or more identification sensors that a correct patient, a correct infusate, or a correct dosage has not been identified, and determination that a full dosage has been administered to a patient.

Furthermore, an identifier, such as a bar code or RF tag can include information about the origin of an infusate, the transportation of an infusate, and any transactions involving the infusate. Thus, the identification sensors may further be configured to confirm drug pedigree. In a clinical setting, medical personnel may use the same device for more than one user. An identifier, such as a bar code or RF tag may be attached to a patient. The identification sensor can be configured to identify a particular patient. If the intended patient is not identified, the smart device may be configured to prevent administration of the fluid. In one embodiment, the device may include a camera and perform facial recognition to identify the authorized user. An application running on the infusion device can direct a user to take a facial picture using the camera. The application can further provide visual indicators on a touch display to assist the user in aligning their face with the camera. The user may then take a facial picture, which can be transmitted to the computing module of the infusion device. At the computing module, the facial picture can be compared to a database of patient pictures stored in a memory of the infusion device. Alternatively, the facial picture may be transmitted to an external device or server containing a database of patient pictures for comparison.

The infusion device may further include a communication module to allow for connectivity between the infusion device and external devices. This allows information from the infusion device to be transmitted to interested parties including the patient, payers, pharmacies and clinicians. The communication module may be configured to perform short-distance RF communication, such as Bluetooth, BLE, or ZigBee®. The communication module may also be configured to perform long distance wireless communication through cellular protocols such as 3G, 4G/LTE, or WiMax. The communication module may also be configured to automatically connect with the electronic medical records system of a user's care facility. The communication module may also allow a user to engage in real-time communication with a clinician. The infusion device may allow for instant messaging, telephonic communications, or real-time video communication. The infusion device can further be configured to store contact information including phone numbers, e-mail addresses, and instant messaging addresses of clinicians, pharmacies, and emergency services in the memory of the infusion device. The infusion device may further include a location sensor, which can be used to allow a user to contact the nearest emergency services provider.

The infusion device may further include a camera. The camera can allow a user to take a picture or video of his or her face so that a clinician can positively identify the user. The camera may also allow a user to engage in a video conversation with a physician. The physician may then provide treatment or device usage advice to the user and answer any questions the user presents in the course of treatment. The camera may also perform facial recognition to identify and authenticate a user before the system allows the pump to be activated. Similarly, a fingerprint sensor or other input component on the infusion device may be used for authentication. An application running on the infusion device may direct the user to align their finger with one or more visual indicators on the touch display. The infusion device may capture the fingerprint and transmit the fingerprint data to the computing module of the infusion device or to an external device or server. The fingerprint can then be compared to a database of fingerprints to determine if there is a match. Furthermore, various forms of password protection may be utilized to prevent access to the infusion device, including textual and motion based passwords.

The infusion device may further be configured to provide various notifications to a user. The notifications can relate to confirmation of identity, the state of an infusate, the state of an infusion, and the receipt of communication. The notifications can comprise visual notification on the touch display, auditory notification such as a chirp or beep, or tactile notification such as vibration of the infusion device. Although various persons, including, but not limited to, a patient or a healthcare professional, can operate or use illustrative embodiments of the present invention, for brevity an operator, patient or user will be referred to as a "user" hereinafter.

Figure 1B:
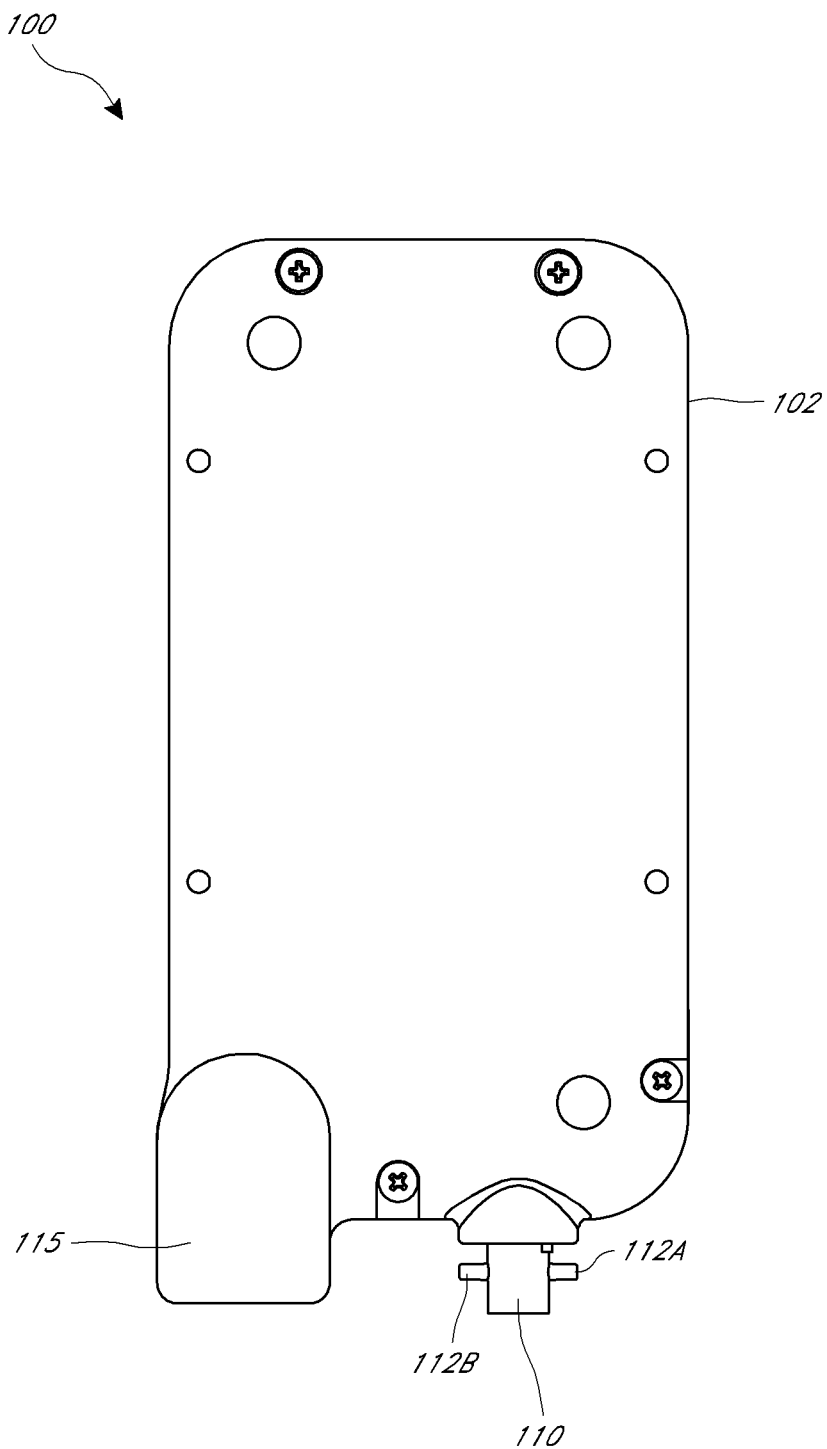
FIG. 1B depicts a rear perspective view of an infusion device in accordance with an illustrative embodiment of the present invention.

FIGS. 1A and 1B depict a front and rear view of an illustrative embodiment of an infusion device 100. The infusion device 100 includes a rectangular housing 102 that is shaped to hold components of the infusion device 100. Positioned on a front face of the housing 102 is a touch display 104 that allows a user to enter commands to the infusion device 100. The touch display 104 can use any well-known technology for registering single or multiple touch events and performing predetermined actions based on each touch. The housing also includes a digital camera 175 mounted centrally above the touch display 104 and configured to capture digital images.

Along a lower portion of the housing 102 are the pump components, including a cylindrical infusion pump head 110. The pump head 110 mounts to the infusion device 100 through a pump head connection port 114. The pump head 110 also includes a pair of fluid path connectors 112A,B which are configured to mate with tubing that contains the liquid to be pumped.

Also provided along the lower portion of the housing 102, and adjacent the pump head connection port 114 is an air bubble detector 115.

As shown, the touch display 104, the camera 175, the pump head connection port, and the air bubble detector 115 are located within the housing 102. In some embodiments the housing 102 may comprise a durable material such as plastic or metal. In some embodiments, the housing 102 may be designed to be ergonomically comfortable for the user. In other embodiments, the housing 102 may also include handgrips.

In an illustrative embodiment, a disposable fluid path is aligned to engage with the fluid path connecters 112A,B and the air bubble detector 115. The disposable fluid path may comprise two or more sections of flexible tubing. A section of flexible tubing can extend from the source of the fluid and engage fluid path connector 112A. Another section of flexible tubing can engage fluid path connecter 112B and can be inserted into air bubble detector 115. The other end of the flexible tubing engaged with fluid path connecter 112B can lead to a patient undergoing an infusion treatment.

In an illustrative embodiment, the pump head 110 can comprise a positive displacement pump head, such as a rotary pump head or reciprocating motion based displacement pump head. However, it should be recognized that the pump head 110 is not limited to a rotary pump head, but may comprise any pump head known in the art.

In practice, the pump head 110 would be activated, which would then cause fluid to move along the tubing. The fluid moves from the source of fluid to fluid path connecter 112A. The fluid then enters the pump head 110. Next, fluid is driven by the pump head 110 out of fluid path connecter 112B. The fluid then traverses the flexible tubing connected to fluid path connecter 112B through the air bubble detector 115 and towards the patient.

In one embodiment, the pump head 110 may be removable from the housing 102. The pump head 110 can thereby be configured to work with multiple infusion devices.

Alternatively, the pump head 100 can be disposable. In one embodiment, a driving element can be configured to engage multiple types of pump heads. The housing 102, and all elements incorporated within the housing 102, can be repeatedly used with multiple patients and multiple infusates. In some embodiments, the pump head 110 may come integrated within a disposable fluid path, the entirety of which may then engage with the infusion device in order to administer an infusion.

The air bubble detector 115 may comprise, but is not limited to, an ultrasonic air bubble detector. The infusion device 100 may be configured to prevent the administration of fluid if an air bubble is detected in the fluid path by air bubble detector 115. The air bubble detector 115 may also comprise one or more infusion-related sensors. The one or more infusion related sensors can comprise, but are not limited to, a temperature sensor, motion sensor, optical sensor, Hall effect sensor, flow sensor, and a pressure sensor.

In an illustrative embodiment, the camera 175 can be configured to obtain pictures or video. For example, a picture may be taken of a patient to confirm identity. Video may be used to allow a patient to send a video communication to another party such as a clinician, payer, or pharmacy.

It should be realized that the touch display 104 is configurable to allow for programming of the infusion device 100. The touch display 104 can be used to enter a dosage amount, intervals at which doses should occur, or a rate at which an infusate is administered to a patient. The touch display 104 can also display information to a user related to the condition of the infusate or the state of the infusion event. This information can be detected by one or more infusion-related sensors or identification sensors housed in the interior of the infusion device 100. The information can include, but is not limited to, temperature, pressure, end of dose, rate of dose, presence of air in fluid path, identity of drug, dosage amount of drug, identity of patient, time of infusion, and location of infusion. The touch display 104 may also be configured to allow a user to transmit information from the sensors to other parties including, but not limited to, clinicians, payers, or pharmacies.

The touch display 104 may also be configured to allow a user to communicate with an external device. The touch display 104 can be configured to allow a user to input textual information to transmit that information to an external device. The touch display 104 can further be configured to allow a user to perform database querying by inputting textual information. The touch display 104 may also allow a user to open and view textual communications received from another party. The touch display 104 may also be configured to allow a user to initiate, control, and terminate an audio conversation, video conversation, or real-time textual conversation with another party. In the case of a video conversation, the touch display 104 may display the video received from another party. In one embodiment of the present invention, the touch display 104 may be configured to allow a user to operate the camera 175, to view images obtained using camera 175, and to transmit those images to an external device.

It should be recognized that the touch display 104 is not limited to a touch display, but may comprise any input and display mechanism known in the art. In an illustrative embodiment according to the present invention, touch display 104 may comprise a keyboard and a display screen. In another embodiment, the touch display 104 may comprise a display screen and the operation performed on the screen may be voice controlled. The touch display 104, may include multiple methods of input, including, but not limited to, touch screen, keyboard, and voice control. The infusion device 100 may further include an orientation sensor. The infusion device can be configured to perform specified functions in response to the orientation or movement of the infusion device.

Figure 2:
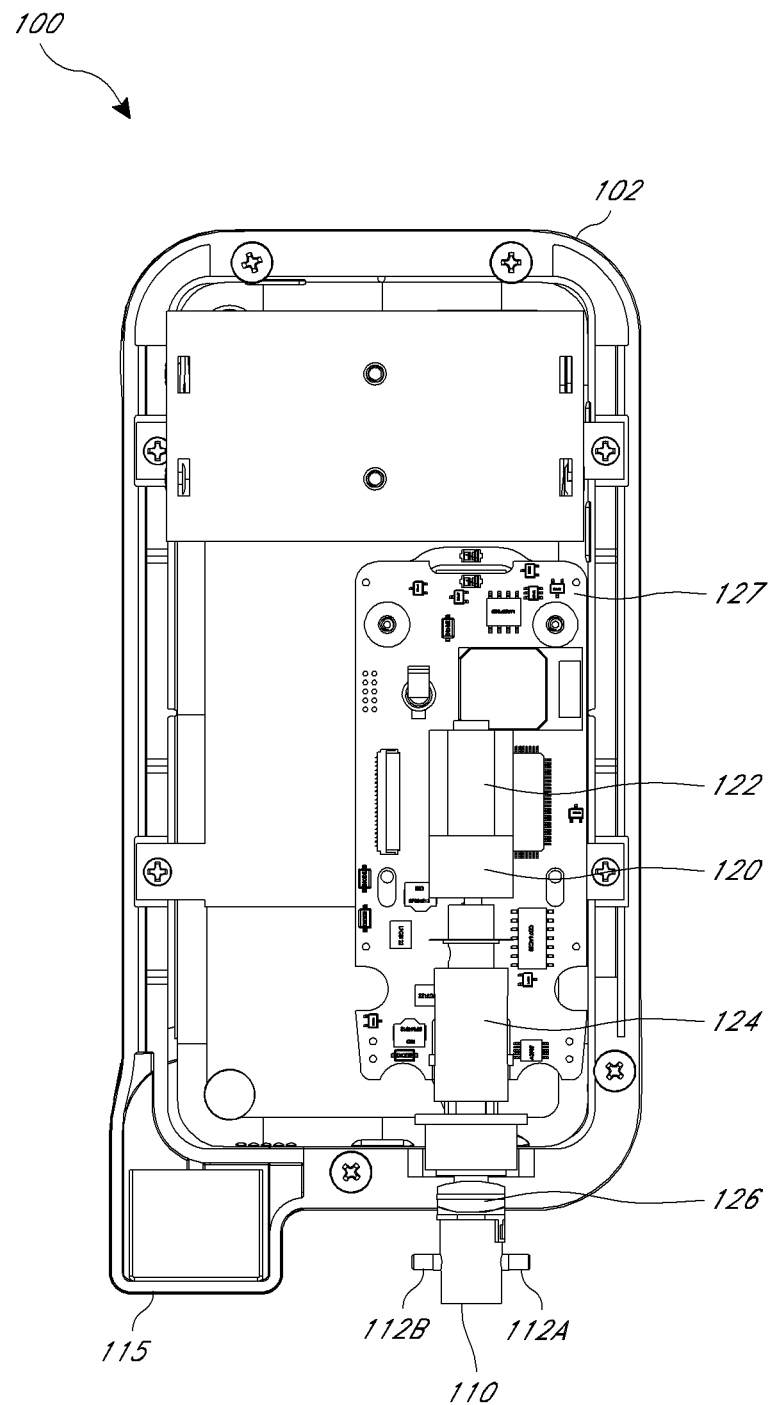
FIG. 2 depicts a cut-away perspective view showing the interior of an infusion device in accordance with an illustrative embodiment of the present invention.

FIG. 2 depicts the interior of an infusion device 100 in accordance with an illustrative embodiment of the present invention. As shown in FIG. 2, the infusion device 100 includes the housing 102, an infusion driving element 120, the pump head 110, the air bubble detector 115, and an electronics package 127.

The driving element 120 includes a motor 122. The motor can comprise any electric motor known in the art, including, but not limited to, a brushed direct current (DC) electric motor, a brushless motor, a stepper motor, a servomotor, a gearmotor, a hollow shaft motor, or a shaftless motor. The driving element 120 further includes a shaft 124 and a pump head connection 126

In operation, when the motor 122 is actuated, the driving element 120 causes rotary or reciprocal motion within the pump head 110. The rotary or reciprocal motion within the pump head 110 causes the displacement of fluid along a disposable fluid path.

The electronics package 127 may comprise one or more infusion-related sensors, one or more identification sensors, a power module, a communication module, a computing module, a location module, and a memory.

Figure 3:
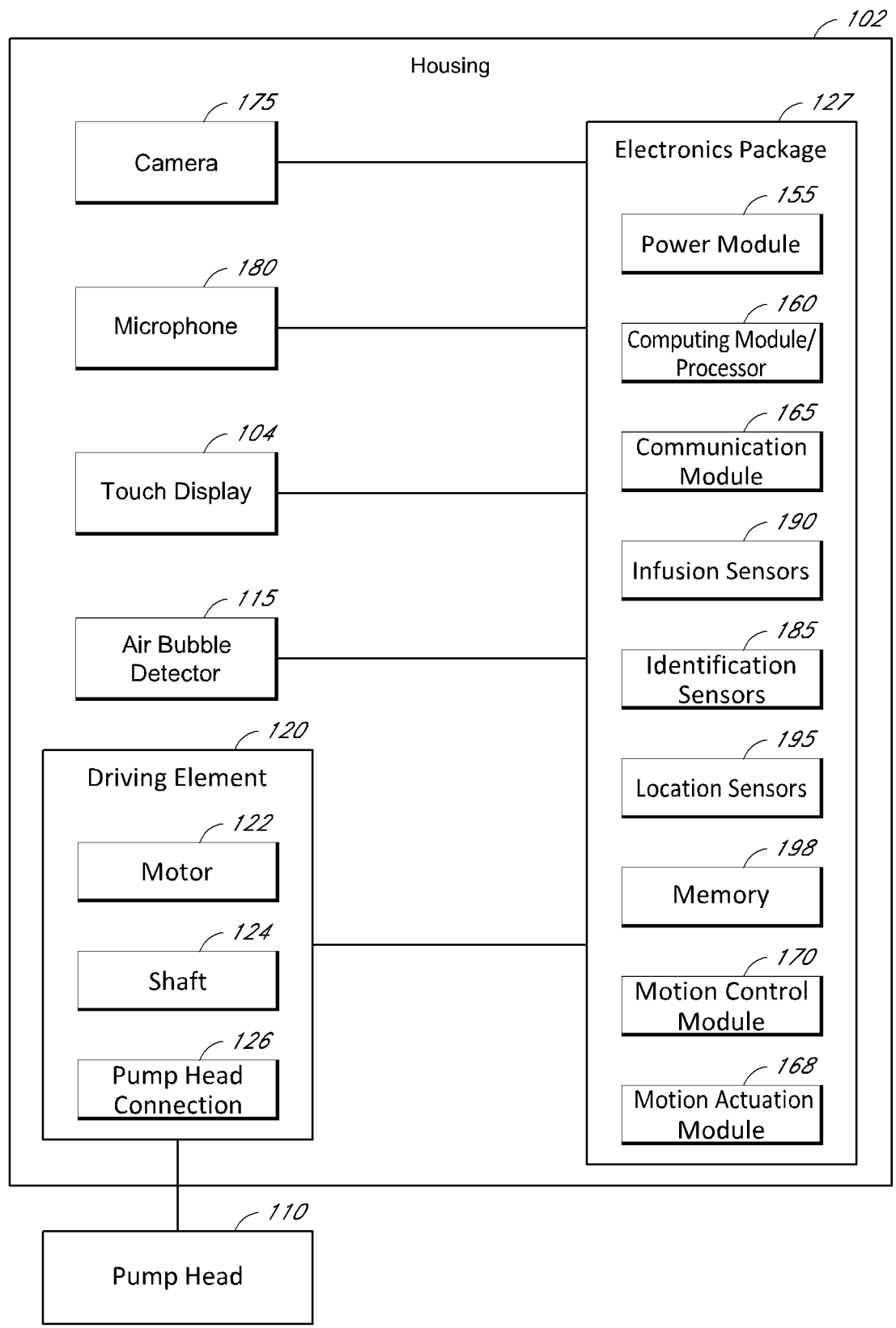
FIG. 3 depicts a schematic view of an infusion device in accordance with an illustrative embodiment of the present invention.

FIG. 3 depicts a schematic view of the infusion device 100. The infusion device 100 comprises the housing 102, the infusion driving element 120, the pump head 110, the camera 175, a microphone 180, the touch display 104, the air bubble detector and the electronics package 127. The infusion driving element 120 further comprises the motor 122, the shaft 124, and the pump head connection 126. The electronics package 127 further comprises a power module 155, a computing module 160, a communication module 165, a motion actuation module 168, a motion control module 170, one or more identification sensors 185, one or more infusion sensors 190, a location module 195, and a memory 198. The computing module 160 may contain one or more microprocessors.

The housing 102 houses the infusion driving element 120, the camera 175, the microphone 180, the touch display 104, the air bubble detector 115, and the electronics package 127. The pump head 110 engages the pump head connection 126 of the infusion driving element 120.

The infusion driving element 120, the pump head 110, the camera 175, the microphone 180, the touch display 104, the air bubble detector 115, the infusion sensors 190, the identification sensors 185, the location sensors 195, the motion control module 170, and the motion actuation module 168 are in communication with the computing module 160. The computing module 160 is further in communication with the memory 198 and the communication module 165.

The housing 102 may comprise one or more pieces that can separately, partially or fully enclose one or more of the infusion driving element 120, the pump head 110, the camera 175, the microphone 180, the touch display 104, the air bubble detector 115, and the electronics package 127. In an illustrative embodiment, the housing 102 can be adapted to include openings for access to features of the infusion device including, but not limited to, the touch display 104, the camera 175, the microphone 180, the air bubble detector 115, buttons, keyboards, screens, interfaces, plugs, jacks, sockets, and speakers. The housing 102 may be further adapted to include room for wires, cords, or any other connection elements that may be attached to the infusion device 100.

In operation, the infusion device 100 allows for the programming of the infusion device using the touch display 104. A user can input a plurality of infusion parameters including, but not limited to, fluid to be administered, amount of dose, rate of dose administration, and intervals at which the dose is to be administered. In response, the programmed data is transmitted to the computing module 160. The computing module 160 then performs on-board processing to determine if the programmed infusion parameters are within a safe and effective range. If the programmed parameters are within a safe and effective range, the device may be ready for infusion.

In some embodiments, the infusion device will commence infusion when it is found that the programmed parameters are within a safe and effective range. The computing module 160 can transmit a signal indicative of instructions to the motor 122 of the infusion driving element 120. The instructions can include, but are not limited to, a start command, a stop command, a direction command, and a speed command. In response, the infusion element 120 can administer infusion in accordance with the programmed parameters.

In other embodiments, a notification may be transmitted to the touch display 104 stating that the programmed parameters are acceptable, and then a further step must be taken to initiate infusion. For example, a button on the touch display 104 can be engaged to initiate infusion. The infusion device 100 can also be configured to allow for programming from an external device. In operation, an external device can transmit programming data to the communication module 165. The communication module 165 can then transmit the programming data to the computing module 160. In an illustrative embodiment, the infusion device can also be configured to allow for programming using the microphone 180. The microphone 180 can transmit audio data to the computing module 160. The computing module 160 may contain speech recognition software. The computing module 160 may then translate the audio data in to programmed parameters.

The touch display 104 can also be configured to provide for the transmission of data to an external device. For example, a textual message can be entered using the touch display 104. The textual message can then be transmitted to the communication module 165. After receiving the textual message, the communication module 165 can be configured to transmit the textual message to an external device. The touch display 104 can also be configured to display data transmitted from an external device and received at the communication module 165.

The identification sensors 185 can include, but are not limited to an RF tag reader or a bar code scanner. A care facility may attach an RF tag or bar code to a patient on, for example, a wristband. The identification sensors 185 can detect the identity of the RF tag or bar code on a patient and transmit that data to the computing module 160. The computing module 160 can be configured to compare the identification information from the identification sensors 185 to information programmed into the infusion device 100. If the identity of the patient is not confirmed, the computing module 160 can be configured to prevent infusion from occurring. In response to confirming or not confirming the identity of a patient, the computing module 160 can also be configured to transmit a message to the touch display 104. The touch display may be configured to display a state of confirmation including confirmed, not confirmed, or error. In an illustrative embodiment, the infusion device 100 can further transmit a message to an external device through the communication module 165 stating that identity is confirmed or not confirmed.

In an illustrative embodiment according to the present invention, the infusion device 100 can be configured to confirm the identity of the patient prior to commencing infusion. For example, one or more identification sensors 185 can be configured to confirm the identity of a patient. In an illustrative embodiment, the camera 175 may also be configured to confirm the identity of a patient. The camera 175 can capture picture or video of a patient. The image data captured by the camera 175 can be transmitted to the computing module 160. The computing module 160 can be configured to perform on-board processing to determine if the image data captured by the camera matches an image of the patient in a database. If the identity of the patient is not confirmed, the computing module 160 can be configured to prevent infusion from occurring. In an alternative embodiment, the image data can be transmitted to the communication module 165. From the communication module 165, the image data can be transmitted to an external device. In an illustrative embodiment, the image data is transmitted to a treating clinician who will confirm the identity of the patient. Alternatively, the image data can be compared to an image of a patient in a database at the external device. In response to confirming or not confirming the identity of a patient, the computing module 160 can also be configured to transmit a message to the touch display 104. The touch display may be configured to display a state of confirmation including confirmed, not confirmed, or error.

In an illustrative embodiment the one or more identification sensors 185 can also be configured to confirm the identity of an infusate. An infusate may be labeled with an RF tag or bar code. The identification sensors 185 can detect the identity of the RF tag or bar code on the infusate and transmit that data to the computing module 160. The computing module 160 can be configured to compare the identification information from the identification sensors 185 to information programmed into the infusion device 100. If the identity of the infusate is not confirmed, the computing module 160 can be configured to prevent infusion from occurring. In response to confirming or not confirming the identity of an infusate, the computing module 160 can also be configured to transmit a message to the touch display 104. The touch display may be configured to display a state of confirmation including confirmed, not confirmed, or error. The label on the infusate can also allow for determination of drug pedigree. In an illustrative embodiment, the infusion device 100 can further transmit a message to an external device through the communication module 165 stating that identity is confirmed or not confirmed.

In an illustrative embodiment the one or more identification sensors 185 can also be configured to confirm that the correct dosage is present in an infusate. The infusate may be labeled with an RF tag or bar code corresponding to the amount of dose present. The identification sensors 185 can detect the identity of the RF tag or bar code on the infusate and transmit that data to the computing module 160. The computing module 160 can be configured to compare the amount of dose identified by the identification sensors 185 to information programmed into the infusion device 100. If the amount of dose is not confirmed, the computing module 160 can be configured to prevent infusion from occurring. In response to confirming or not confirming the amount of dose, the computing module 160 can also be configured to transmit a message to the touch display 104. The touch display 104 may be configured to display a state of confirmation including confirmed, not confirmed, or error. In an illustrative embodiment, the infusion device 100 can further transmit a message to an external device through the communication module 165 stating that the amount of dose is confirmed or not confirmed.

In an illustrative embodiment according to the present invention, the identification sensors 185 may have a writing capability. The identification sensors 185 may be configured to add, modify, or replace data on a label such as an RF tag or bar code. In one embodiment, the RF tag can comprise an NFC type RF tag. In another embodiment the identification sensors 185 may comprise an optical bar code scanner.

The infusion device 100 can be configured to monitor and detect predetermined events and characteristics associated with the use of an infusion device. For example, the infusion device 100 may be configured to detect that an infusate is in condition for infusion prior to commencing infusion. Thus, the infusion sensors 190 can be configured to collect infusion parameter data including, but not limited to temperature, flow, and pressure. The air bubble detector 115 can be configured to detect the presence of air or other gases in a fluid.

In one embodiment, the infusion sensors 190 and the air bubble detector 115 are activated after the computing module 160 receives programed instructions. In response, sensor data is transmitted from the infusion sensors 190 and the air bubble detector 115 to the computing module 160. The computing module 160 then performs on-board processing using an algorithm to determine the state of the infusate. In one embodiment, the computing module 160 determines whether one or more infusion parameters are outside of a defined range. If a determination is made that one or more infusion parameters are outside of a defined range, the computing module 160 may prevent infusion from occurring. The computing module 160 can further transmit data to the touch display 104, and in response, the touch display 104 can display a state of the infusate. Examples of states of the infusate include, but are not limited to, ready for infusion, not ready, within range, outside of range, and error. The computing module 160 can also communicate the state of the infusate data to the communication module 165, and in response, the communication module 165 can transmit the state of the infusate data to an external device.

The one or more infusion sensors 190 and the air bubble detector 115 can further be configured to monitor infusion parameters throughout the administration of infusion. The infusion parameters can be monitored continuously until infusion is complete. Alternatively, the infusion sensors 190 and the air bubble detector 115 can be configured to monitor infusion parameters at defined intervals during infusion. The computing module 160 may terminate infusion or prevent infusion or further infusion from occurring in response to one or more predetermined events. For example, if a determination is made that one or more infusion parameters are outside of a defined range, the computing module 160 may terminate infusion and prevent further infusion from occurring. Other predetermined events include detection that a full dose has been administered based on the infusion parameters or detection that identification sensor data does not match the infusion parameters. The computing module 160 may further transmit data to the touch display 104 or to an external device using communication module 165 to provide notification of termination of infusion.

In one illustrative embodiment, the one or more infusion sensors 190 can detect end of dose. After end of dose is determined, the sensors 190 can transmit end of dose data to the computing module 160. The computing module 160 can transmit the end of dose data to the touch display 104, and in response, the touch display can be configured to display that end of dose was achieved. The computing module 160 can further transmit the end of dose data to the communication module 165. In response to receiving the end of dose data, the communication module 165 can transmit the end of dose data to an external device.

In one illustrative embodiment, the one or more infusion sensors 190 can also detect the amount of infusate delivered to a patient. The amount of infusate data can then be transmitted to the touch display 104 or to an external device through the communication module 165.

In an illustrative embodiment according to the present invention, the sensors 190 may comprise a temperature sensor. In one embodiment, the temperature sensor can be used to verify cold-chain storage and distribution. In one embodiment, the temperature sensor can be used to detect the ambient temperature when an infusion event occurs.

In an illustrative embodiment, the sensors 190 may comprise, an optical sensor including, but not limited to an IR sensor. The optical sensor can detect data relevant to end of dose. In another embodiment, the one or more sensors 190 can detect dose administration speed.

In an illustrative embodiment, the sensors 190 may comprise a flow sensor. The flow sensor can detect dose administration speed.

In an illustrative embodiment, the sensors 190 may comprise a pressure sensor. The pressure sensor can measure the pressure in a disposable fluid path. This data can be relevant for calculating flow speed.

In an illustrative embodiment, the sensors 190 may comprise a Hall effect sensor. The Hall effect sensor can detect data relevant to end of dose.

In an illustrative embodiment, the sensors 190 may detect the type of infusate in the infusion device.

In an illustrative embodiment, the camera 175 of the infusion device 100 can further be configured to provide video communication to an external device. The camera 175 can be configured to record video. The microphone 180 can be configured to record sound. The camera 175 and microphone 180 can transmit video and audio data to the communication module 165. The communication module 165 can transmit the video and audio data to an external device.

The infusion device 100 can also be configured to receive video communication from an external device. The communication module 165 can receive video and audio data from an external device. The video data can be transmitted to the touch display 104 and the sound data can be transmitted to the microphone 180. The touch display 104 can display the video corresponding to the video data and the microphone 180 can emit the sound corresponding to the sound data. Thus, the infusion device 100 can allow a patient to communication with a clinician, payer, or pharmacy through video communication. In one alternative embodiment, the infusion device 100 can be configured to provide for a solely audio communication.

The communication module 165 can be connected to a network by wired or wireless communication, cell communication, Bluetooth®, ZigBee®, LAN, WLAN, RF, IR, or any other communication method or system known in the art. The communication module 165 can communicate with a mobile device, a home health monitor, a computer, a server, or any other external device. This allows device data to be transmitted to users, payers, pharmacists, physicians, nurses, family members or any other desired parties. The communication module 165 may be configured to perform short-distance RF communication, such as Bluetooth, BLE, or ZigBee®. The communication module 165 may also be configured to perform long distance wireless communication through cellular protocols such as 3G, 4G/LTE, or WiMax. The infusion device 100 can further comprise one or more ports or sockets to allow for a wired connection between the infusion device 100 and an external device such as a mobile device or computer. Data may further be transferred from the infusion device 100 to an external device using a data storage device such as a flash drive or memory card.

The communication module 165 may further be configured to communicate with the electronic medical records of a medical facility. The communication module 165 can transmit infusion data to the electronic medical records system. The communication module 165 can also be configured to receive patient data from the electronic medical records system, which can allow a user to ascertain an infusate and dosage to administer.

In an illustrative embodiment according to the present invention, the power module 155 can comprise a rechargeable battery. In one embodiment, the power module 155 can include an external switch. The power module 155 can supply power to the infusion device for multiple hours.

In an illustrative embodiment according to the present invention, the location sensors 195 can be configured to determine the place and time of an infusion event. In one embodiment, the location sensors 195 comprise GPS technology. The place and time data can be transmitted to an external device or stored in the memory 198 of the infusion device 100.

In an illustrative embodiment according to the present invention, the memory 198 can be configured to store data including, but not limited to, programmed infusion instructions, infusion parameter data, identification parameter data, location and time data, verification of dose data, textual transmission data, video transmission data, and audio transmission data.

In an illustrative embodiment according to the present invention, the motion control module 170 and the motion actuation module 168 can be configured to regulate the motion of the infusion driving element 120.

The computing module 160 may further be configured to perform database querying and cross verification, digital counting, and integration of voltage and current signals to drive the infusion process.

The infusion device 100 may further comprise software that provides an interface on the touch display 104. The software can be packaged as an application or series of applications such as those used in portable consumer mobile devices. The application or series of applications can provide functionality to connect the pump to external devices, allowing for the transmission of data to electronic medical records, clinicians, pharmacies, and payers. The application can also provide for database querying and cross verification, digital counting, and the integration of voltage and current signals to drive the infusion process.

An application can also be configured to provide for simple programming of the infusion device 100. In an illustrative embodiment, the touch display 104 can display a set of infusion related factors including, but not limited to, the identity of the patient, the fluid to be administered, amount of dose, rate of dose administration, and intervals at which the dose is to be administered. The application may then allow a user to input values for each factor. The user may input values by typing the corresponding letters and numbers using the touch display. The values may then be compared to a database, for example, of different potential infusates. Alternatively, the user may select the values from a list of values. A list of values may be updated wirelessly through the communication module 165.

Figure 4:
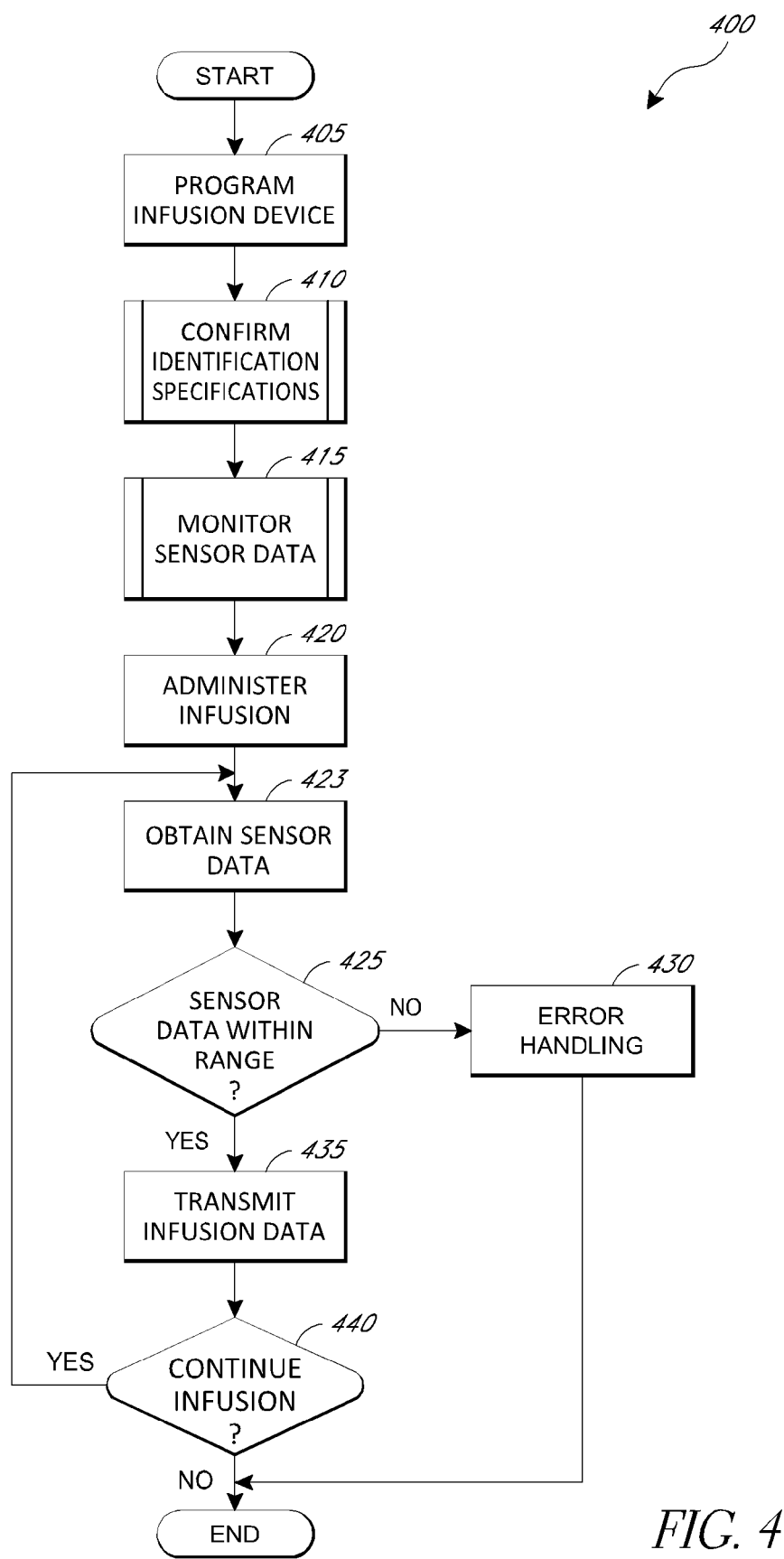
FIG. 4 depicts a flowchart of an embodiment of a method of operating an infusion device in accordance with an illustrative embodiment of the present invention.

FIG. 4 depicts a flowchart of one embodiment of a process operating an infusion device such as infusion device 100 depicted in FIGS. 1-3. The process 400 begins at a start step, and then moves to a step 405 wherein an infusion device is programmed, such as infusion device 100 depicted in FIGS. 1-3. In one embodiment, the infusion device may be programmed using a touch display such as touch display 104 depicted in FIGS. 1-3. In an alternative embodiment, the infusion device may be programmed remotely by transmitting instructions to a communication module, such as communication module 165 depicted in FIG. 3.

After the device is programmed, the process 400 moves to a process step 410, wherein identification specifications are confirmed by one or more identification sensors. The functions of process step 410 will be explained in further detail below with reference to FIG. 5. After the identification specifications are confirmed, the process 400 moves to a process step 415, wherein sensor data is monitored by one or more infusion related sensors prior to infusion. The sensor data can be monitored to determine if one or more measurements are within programmed infusion parameters or safety parameters. The function of process step 415 will be explained in further detail below with reference to FIG. 6.

After the sensor data has been monitored at process step 415, the process 400 moves to a step 420, wherein an infusion begins to be administered by the infusion device, such as infusion device 100 depicted in FIGS. 1-3.

After the infusion begins to be administered, the process 400 moves to a step 423, wherein sensor data is obtained from one or more sensors in the infusion device, such as the infusion sensors 190 and the air bubble detector 115 depicted in FIG. 3.

After the sensor data is obtained, the process 400 moves to a decision step 425, wherein a determination is made whether sensor data from one or more of the sensors is within a defined range. The defined range for one or more of the sensors may be based on infusion parameters input by a user. The defined range for one or more of the sensors may also be based on preprogrammed safety parameters. The determination can be performed by a computing module, such as computing module 160 depicted in FIG. 3.

If a determination is made at decision step 425 that the sensor data for one or more of the sensors is not within a defined range, the process 400 moves to a step 430, wherein error handling occurs. In this step, sensor data can be transmitted to an external device or to a display on the infusion device. A computing module, such as computing module 160 depicted in FIG. 3, may also terminate infusion and prevent further infusion from occurring until the sensor data is within a defined range.

If a determination is made at decision step 425 that the sensor data for one or more of the sensors is within a defined range, then the process 400 moves to a step 435, wherein infusion data is transmitted to an external device through a communication module, such as communication module 165 depicted in FIG. 3. The infusion data can also be transmitted to a display on the infusion device. The infusion data can include the sensor data from one or more sensors such as the infusion sensors 190 and air bubble detector 115, identification information, time information, and amount of dosage information. In another embodiment, a state of the infusate can be determined by a computing module. The determined state can then be transmitted to an external device or to the display.

After transmitting infusion data, the process 400 moves to a decision step 440, wherein a determination is made whether infusion continues to occur. This determination may be performed by one or more sensors including, but not limited to, an optical sensor or Hall effect sensor. If a determination is made that infusion continues to occur, the process 400 returns to step 423 to continue to obtain sensor data. If a determination is made at decision step 440 that infusion does not continue to occur, the process 400 concludes at an end step.

Figure 5:
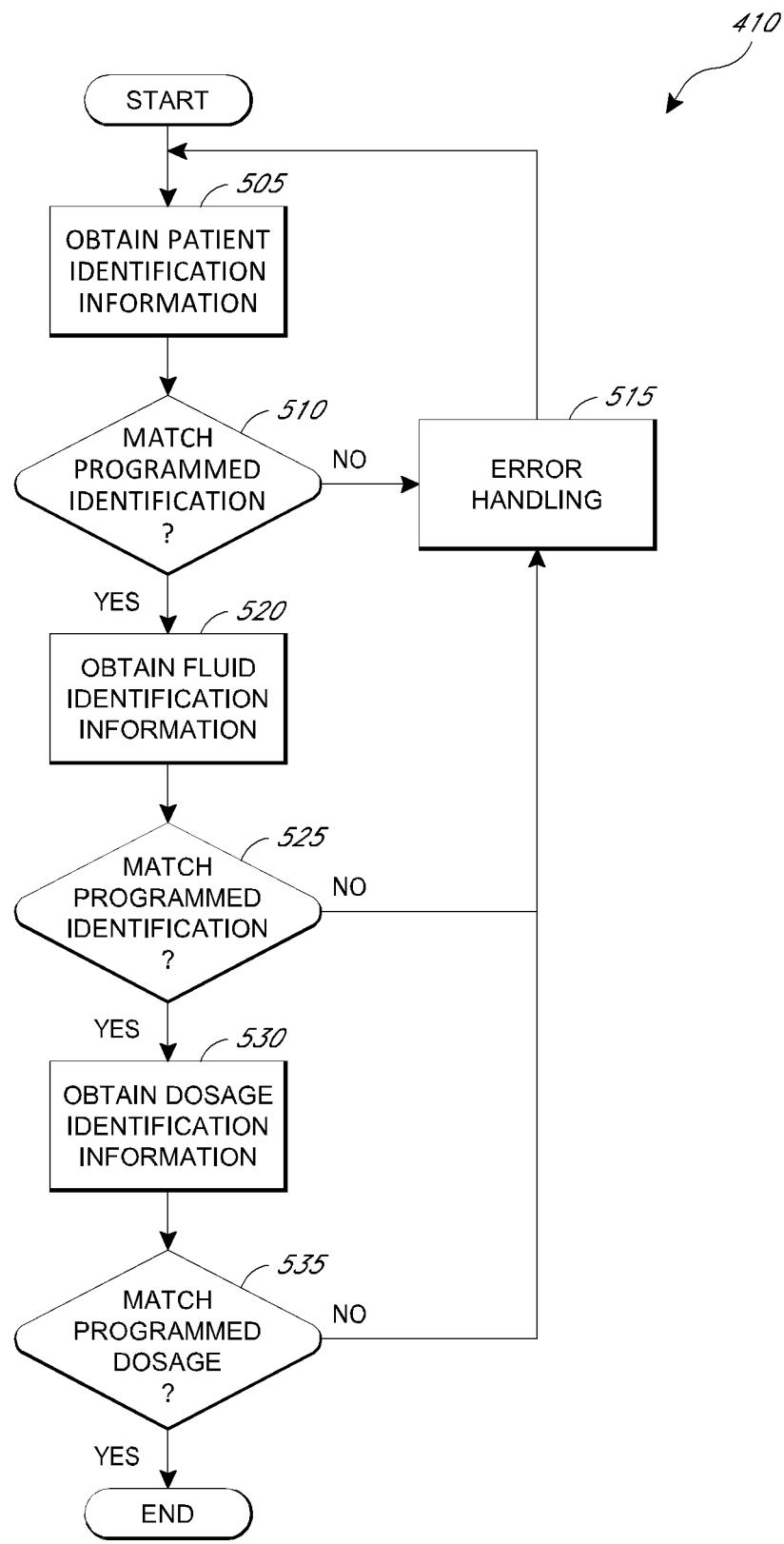
FIG. 5 depicts a flowchart of an embodiment of confirming identification parameters in an infusion device in accordance with an illustrative embodiment of the present invention.

FIG. 5 depicts a flowchart of a process 410 of an illustrative embodiment according to the present invention of confirming identification specifications. The process 410 begins at a start step, and then moves to a step 505, wherein patient identification information is obtained. The patient identification can be performed by one or more identification sensors, such as identification sensors 180 depicted in FIG. 3. Identification can also be performed using a camera, such as camera 175 depicted in FIGS. 1-3.

After obtaining patient identification information, the process 410 moves to a decision step 510, wherein a determination is made whether the patient identification information matches the patient information programmed to the infusion device. If a determination is made that the patient identification information does not match the programmed patient information, the process 410 moves to a step 515, wherein error handling occurs. At step 515, a notification may be transmitted to an external device or to a display on the infusion device, notifying that there was not a match. After the notification is transmitted, the process 410 returns to step 505 to continue to obtain patient identification information.

If a determination is made at decision step 510 that the patient identification information matches the programmed patient information, the process 410 moves to a step 520, wherein fluid identification information is obtained. The fluid identification can be performed by one or more identification sensors.

After obtaining fluid identification information, the process 410 moves to a decision step 525, wherein a determination is made whether the fluid identification information matches the fluid information programmed to the infusion device. The determination can be performed by a computing module such as computing module 160 depicted in FIG. 3. If a determination is made that the fluid identification information does not match the programmed fluid information, the process 410 moves to a step 515, wherein error handling occurs. At step 515, a notification may be transmitted to an external device or to a display on the infusion device, notifying that there was not a match. After the notification is transmitted, the process 410 returns to step 505 to continue to obtain patient identification information.

If a determination is made at step 525 that the fluid identification information matches the programmed fluid information, the process 410 moves to a step 530, wherein dosage identification information is obtained. In this step, the amount of dose available is obtained. The dosage identification can be performed by one or more sensors.

After obtaining fluid identification information, the process 410 moves to a decision step 535, wherein a determination is made whether the dosage identification information matches the dosage information programmed to the infusion device. The determination can be performed by a computing module such as computing module 160 depicted in FIG. 3. If a determination is made that the dosage identification information does not match the programmed dosage information, the process 410 moves to a step 515, wherein error handling occurs. At step 515, a notification may be transmitted to an external device or to a display on the infusion device, notifying that there was not a match. After the notification is transmitted, the process 410 returns to step 505 to continue to obtain patient identification information.

If a determination is made at step 535 that the dosage identification information matches the programmed dosage information, the process 410 concludes at an end step.

Figure 6:
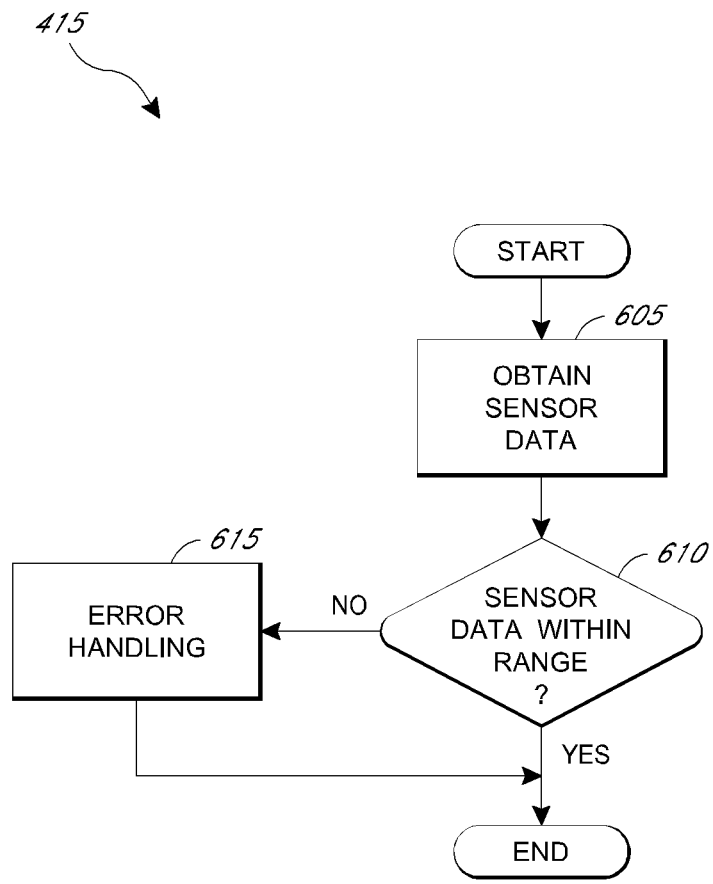
FIG. 6 depicts a flowchart of an embodiment of monitoring sensor parameters in an infusion device in accordance with an illustrative embodiment of the present invention.

FIG. 6 depicts a flowchart of a process 415 of an illustrative embodiment according to the present invention of monitoring sensor data prior to infusion. The process 415 begins at a start step, and then moves to a step 605, wherein sensor data is obtained from one or more sensors in the infusion device, such as the infusion sensors 190 and the air bubble detector 115 depicted in FIG. 3. The process 415 then moves to a decision step 610 wherein a determination is made whether sensor data from one or more sensors of the sensors is within a defined range. The defined range for one or more of the sensors may be based on infusion parameters input by a user. The defined range for one or more of the sensors may also be based on preprogrammed safety parameters. If a determination is made that the sensor data from one or more of the sensors is within a defined range, the process 415 concludes at an end step.

If a determination is made that the sensor data from one or more sensors of the sensors is not within a defined range, the process 415 moves to a step 615, wherein error handling occurs. At step 615, a notification may be transmitted to an external device or to a display on the infusion device, notifying that the sensor data is not within a defined range. In one embodiment, the computing module may prevent an infusion from occurring, unless the sensor data is recalculated and the sensor data from one or more of the sensors is within the defined range. After error handling occurs, the process 415 concludes at an end step.

Figure 7A:
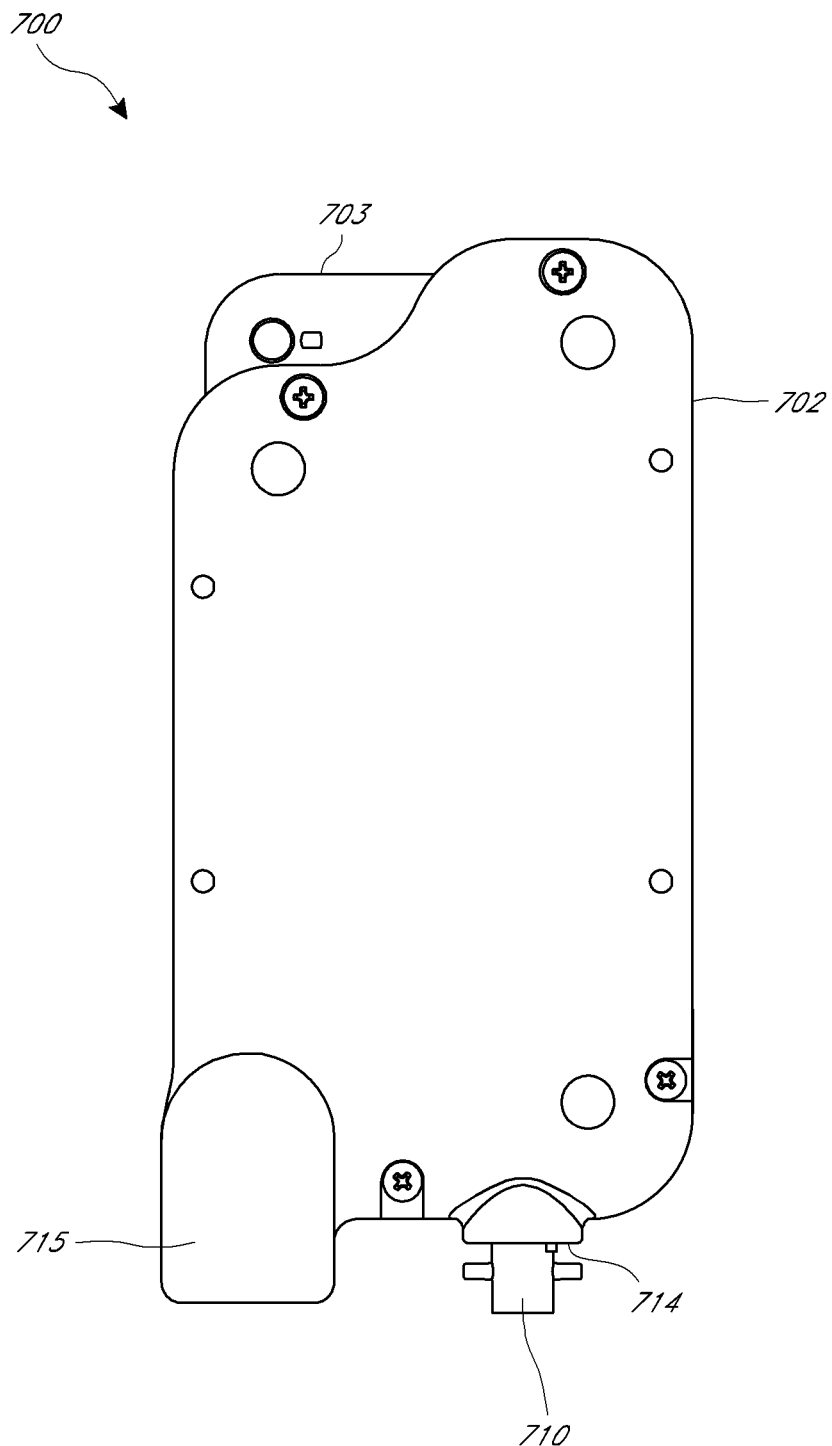
FIG. 7A depicts an infusion device in accordance with an illustrative embodiment of the present invention.
Figure 7B:
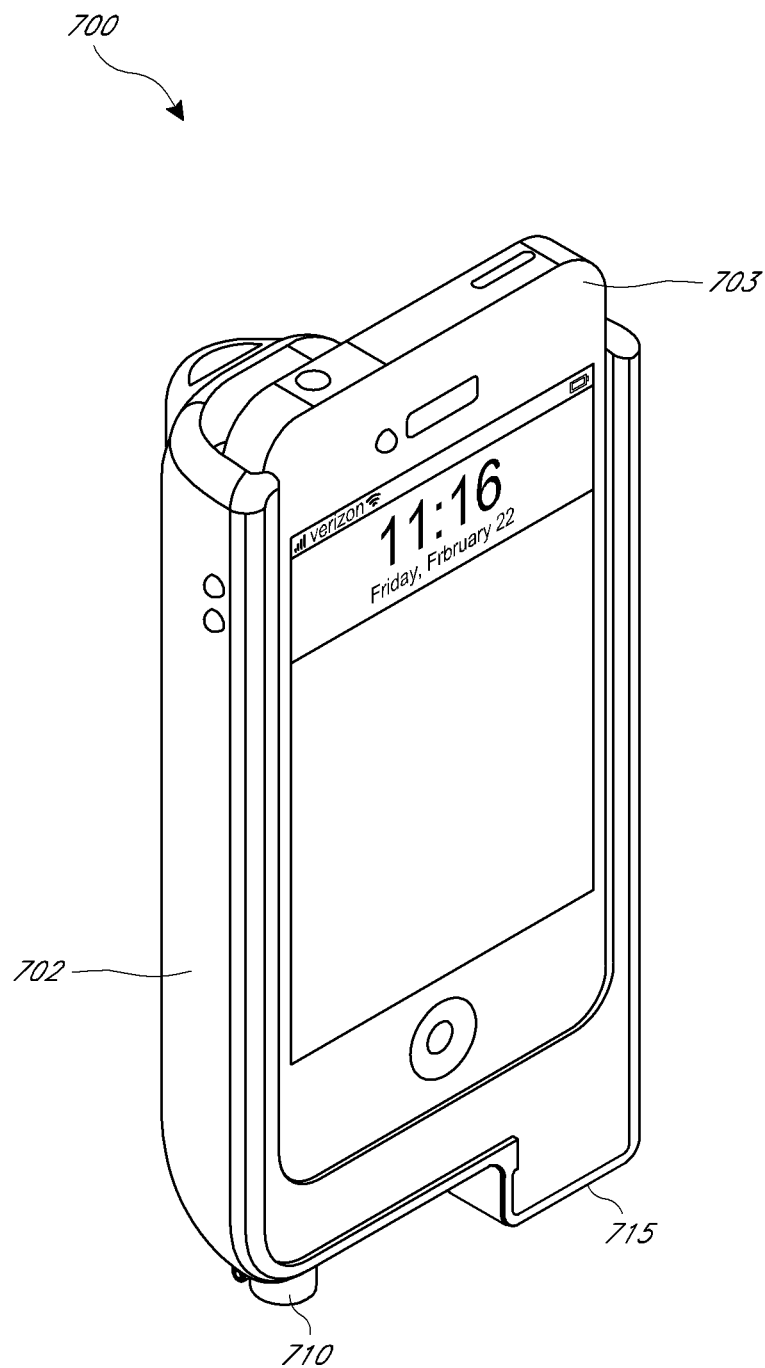
FIG. 7B depicts an infusion device in accordance with an illustrative embodiment of the present invention.

FIGS. 7A and 7B depict an alternate embodiment of an infusion device 700 in accordance with an illustrative embodiment of the invention. The infusion device 700 includes a housing sleeve 702, a mobile device 703 and a pump head 710. The housing sleeve 702 can be configured to house an infusion driving element, such as infusion driving element 120 depicted in FIG. 1. The housing sleeve 702 may further comprise a pump head connection port 714. The pump head 710 can be attached to a pump head connection (not shown) of an infusion driving element (not shown) through the pump connection port 714. The housing sleeve 702 may further be configured to house an air bubble detector 715. The housing sleeve may further comprise a connection module configured to connect the housing sleeve 702 to the mobile device 703.

The mobile device 703 may be comprise one or more of the modules and components included in the infusion device 100 as depicted in FIGS. 1-3, such as a camera, a microphone, a touch display, a power module, a computing module, a communication module, one or more infusion sensors, one or more identification sensors, one or more location sensors, a memory, a motion control module, and a motion actuation module.

In an illustrative embodiment according to the present invention, the housing sleeve 702 is adapted to receive and mount the mobile device 703. The housing sleeve 702 can be configured to provide a structural coupling between the infusion driving element and the mobile device 703.

In one embodiment, the housing sleeve 702 is made of a flexible material to allow the portions of the sleeve that do not contain electrical components to bend or fold for easier transport of the housing sleeve 702. The housing sleeve 702 can also contain rigid sections to provide protection for the driving element and air bubble detector, as well as the mobile device 703. The housing sleeve 702 may further include one or more protrusions, ridges, recesses, curves, edges, lips, openings, rough surfaces, or other physical features to facilitate gripping of the infusion device 700. The housing sleeve 702 may further be configured to engage with a cell phone holder or clip.

In an illustrative embodiment according to the present invention, the housing sleeve 702 is adapted to include openings for access to mobile device features including, but not limited to, buttons, keyboards, screens, interfaces, plugs, jacks, sockets, speakers, and cameras. In an illustrative embodiment according to the present invention, the housing sleeve 702 is further adapted to include room for wires, cords, or other connection elements to the mobile device.

In an illustrative embodiment according to the present invention, the connection module of the housing sleeve is connectable to the mobile device 703. The connection module can include any wired or wireless mobile device connector known in the art, including, but not limited to USB, USB Mini-A, USB Mini-B, Micro-USB, 8-pin, 9-pin and 30-pin connectors, and electromagnetic couplings. In one embodiment, the connection module includes any wireless connection module connectable to a mobile device known in the art, including, but not limited to, radio frequency, Bluetooth®, infrared, Wi-Fi or cellular connection modules. In an illustrated embodiment, the connection module is adapted to provide electrical power from the mobile device 703 to the infusion driving element of the housing sleeve 702. In an illustrated embodiment, the connection module is further adapted to provide electrical power to the air bubble detector 715 from the mobile device 703.

In an illustrated embodiment according to the present invention, the housing 702 may further comprise a controller interface (not shown). The controller interface can be adapted to receive a signal from the mobile device 703 through the connection module. The controller interface can translate digital or analog electrical signals input from the mobile device 703 through the connection module, into electric signals, including, but not limited to, digital or analog electrical signals output to the infusion driving element. In an illustrative embodiment, the signals are indicative of instruction for a motor of the infusion driving element, including, but not limited to, a start command, a stop command, a direction command, and a speed command.

The infusion device 700 can be configured to perform the same functions as described above with respect to infusion device 100 depicted in FIGS. 1-3, including, but not limited to, programming of the infusion device 700, confirming the identity of a patient, fluid, or dosage amount, detecting that a fluid is in condition for infusion and that infusion is properly occurring, preventing infusion from occurring if sensor data is not within defined parameters, detecting end of infusion, communicating data to an external device, recording a place, date, and time at which an infusion event occurs, and displaying data on a display of the infusion device 700.

Implementations disclosed herein provide systems, methods and apparatus for a smart portable infusion pump. One skilled in the art will recognize that these embodiments may be implemented in hardware, software, firmware, or any combination thereof.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

Headings are included herein for reference and to aid in locating various sections. These headings are not intended to limit the scope of the concepts described with respect thereto. Such concepts may have applicability throughout the entire specification.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:
1. A device for delivery of fluid, comprising:
an infusion pump driving element;

a removable pump head connected to the driving element and capable of displacing fluid along a disposable fluid path;

a housing at least partially enclosing the infusion pump driving element, wherein the housing comprises a sleeve configured to mate with a cellular telephone;

a processor configured to read programmed infusion parameters, wherein the processor is further configured to activate the infusion pump driving element in accordance with the programmed infusion parameters; and one or more environmental sensors, wherein the processor is further configured to read data from the environmental sensors and prevent infusion if a predetermined event occurs.

2. The device of claim 1, wherein the removable pump head is designed to be a disposable pump head.

3. The device of claim 2, wherein the pump head comprises attachment points for tubing.

4. The device of claim 1, further comprising a touchscreen configured to receive electronic input from a user.

5. The device of claim 1, wherein the one or more environmental sensors are temperature, flow, pressure, or air sensors.

6. The device of claim 5, wherein the one or more environmental sensors is an air sensor, wherein the air sensor is configured to detect the presence of air within tubing connected to the pump head.

7. The device of claim 6, wherein the air sensor is mounted to the housing that encloses the infusion pump driving element.

8. The device of claim 1, further comprising an identification sensor configured to identify a patient, an infusate, or the dosage amount of an infusate.

9. The device of claim 8, wherein the identification sensor comprises a digital camera or fingerprint sensor.

10. The device of claim 9, wherein the identification sensor comprises a digital camera and the device is configured to perform facial recognition on images captured with the digital camera.

11. The device of claim 9, wherein the identification sensor is part of the cellular telephone mated to the sleeve.

12. The device of claim 1, wherein the predetermined event comprises detecting that environmental data is outside of a defined range or detecting administration of a full dosage amount.

13. A method of operating a programmable infusion device, comprising:
providing a portable infusion device configured to administer an infusate and comprising infusion parameters, the portable infusion device comprising a sleeve mated with a cellular telephone;
monitoring environmental data via one or more environmental sensors,
administering the infusate in accordance with the infusion parameters;
processing the environmental data to determine if a predetermined event has occurred; and
terminating infusion in response to the occurrence of the predetermined event.

14. The method of claim 13, further comprising transmitting data from the one or more environmental sensors to an external device.

15. The method of claim 13, further comprising obtaining identification data via one or more identification sensors for one or more of a patient and the infusate.

16. The method of claim 15, wherein the one or more identification sensors comprise one or more of a digital camera or fingerprint sensor.

17. The method of claim 13, wherein the one or more environmental sensors comprise one or more of temperature, flow, pressure, or air sensors.

18. The method of claim 13, wherein the infusion parameters are provided by receiving an electronic input on a touch screen of the portable infusion device.

19. The method of claim 13, further comprising displacing the infusate along a disposable fluid path.

20. The method of claim 13, wherein the predetermined event comprises one or more of detection of environmental data outside of a defined range and detection of administration of a full dosage amount.

21. The device of claim 1, further comprising a connection module electrically connected to the infusion pump driving element and configured to receive data from the cellular telephone.

* * * * *